United States Patent [19]
Thill et al.

[11] Patent Number: 5,437,642
[45] Date of Patent: Aug. 1, 1995

[54] FREE FLOW PREVENTION SYSTEM FOR INFUSION PUMP

[75] Inventors: Gary A. Thill, Vadnais Heights; Mark A. Toycen, St. Paul; Kent R. Struble, Mahtomedi; Timothy G. Curran, Ramsey, all of Minn.

[73] Assignee: Minnesota Mining and Manufacturing Company, St. Paul, Minn.

[21] Appl. No.: 70,497

[22] Filed: Jun. 1, 1993

Related U.S. Application Data

[63] Continuation of Ser. No. 690,819, Apr. 23, 1991, abandoned.

[51] Int. Cl.⁶ .............................................. A61M 1/00
[52] U.S. Cl. ..................... 604/153; 604/245; 604/246; 604/250; 428/DIG. 12; 428/DIG. 13; 251/9; 417/474; 417/478
[58] Field of Search ............... 128/DIG. 12, DIG. 13, 128/685, 686; 604/30, 31, 34, 150, 151, 153, 131, 245, 246, 250; 251/4, 7, 10, 9; 417/474, 475, 477 A, 477 R, 478, 479, 480, 497, 510

[56] References Cited

U.S. PATENT DOCUMENTS

| | | |
|---|---|---|
| 820,216 | 5/1906 | Leffingwell et al. |
| 1,968,454 | 7/1934 | Hyatt ........................ 251/5 |
| 2,715,905 | 8/1955 | Ogle. |
| 2,722,932 | 11/1955 | Hickey ...................... 604/34 |
| 2,806,482 | 9/1957 | Norris et al. ............... 137/376 |
| 2,832,560 | 4/1958 | Grigsby .................... 251/9 |
| 2,889,848 | 6/1959 | Redmer. |
| 3,216,418 | 11/1965 | Scislowicz. |
| 3,316,935 | 5/1967 | Kaiser et al. |
| 3,390,860 | 7/1968 | Kavanau ................... 251/9 |
| 3,539,081 | 11/1970 | Norton et al. ............. 222/185 |
| 3,698,681 | 10/1972 | Lacey ....................... 251/10 |
| 3,759,483 | 9/1973 | Baxter. |
| 3,822,052 | 7/1974 | Lange ....................... 251/10 |
| 3,942,228 | 3/1976 | Buckman et al. .......... 24/255 |
| 4,091,815 | 5/1978 | Larsen. |
| 4,097,020 | 6/1978 | Sussman .................... 251/10 |
| 4,193,174 | 3/1980 | Stephens ................... 24/249 |

(List continued on next page.)

FOREIGN PATENT DOCUMENTS

| | | |
|---|---|---|
| 0186509 | 7/1986 | European Pat. Off. ........... 604/250 |
| 0205234 | 12/1986 | European Pat. Off. |
| 0319279 | 12/1987 | European Pat. Off. |

(List continued on next page.)

OTHER PUBLICATIONS

AVI480 Infusion Pump With Free-Flow Prevention, 3M Health Care brochure, May 1990.
AVI200A Infusion Pump; 3M Health Care brochure, Nov. 1988.
Gemini Adminstration Sets, IMED brochure, 1987.

*Primary Examiner*—C. Fred Rosenbaum
*Assistant Examiner*—Ronald K. Stright, Jr.
*Attorney, Agent, or Firm*—Gary L. Griswold; Walter N. Kirn; Stephen W. Bauer

[57] ABSTRACT

A free flow prevention system for preventing undesired free flow of fluid through IV tubing of the type used in an infusion pump. The system comprises a spring clip having a base and a spring arm defining a channel adapted to receive the IV tubing. The spring arm is resiliently biased to a closed position in which the IV tubing is squeezed by the spring clip to close the lumen to prevent fluid flow, and the spring arm is movable against the bias to an open position wherein the lumen of the IV tubing is allowed to open to allow flow. The system also includes a clip-opening pin in the infusion pump for moving the spring arm of the clip from its closed position to the open position. The clip-opening pin is movable relative to the spring clip to move the spring arm between an unloading position, in which the clip-opening pin does not hold the spring arm in its open position, and an operating position, in which the clip-opening pin moves the spring arm to its open position and holds the spring arm in the open position.

29 Claims, 5 Drawing Sheets

U.S. PATENT DOCUMENTS

| | | |
|---|---|---|
| 4,230,151 | 10/1980 | Johsson . |
| 4,236,880 | 12/1980 | Archibald . |
| 4,247,076 | 1/1981 | Larkin .................................... 251/7 |
| 4,261,388 | 4/1981 | Shelton . |
| 4,277,226 | 7/1981 | Archibald . |
| 4,322,201 | 3/1982 | Archibald . |
| 4,382,753 | 5/1983 | Archibald . |
| 4,391,600 | 7/1983 | Archibald . |
| 4,410,322 | 10/1983 | Archibald . |
| 4,434,963 | 3/1984 | Russell . |
| 4,460,358 | 7/1984 | Sommerville et al. . |
| 4,519,792 | 5/1985 | Dawe . |
| 4,527,588 | 7/1985 | Tseo et al. . |
| 4,560,378 | 12/1985 | Weiland ............... 604/250 |
| 4,585,441 | 4/1986 | Archibald . |
| 4,585,442 | 4/1986 | Mannes ............... 604/250 |
| 4,586,691 | 5/1986 | Kozlow . |
| 4,589,626 | 5/1986 | Kurtz et al. .................... 251/10 |
| 4,620,564 | 11/1986 | Ekholmer . |
| 4,673,161 | 6/1987 | Flynn et al. .................. 604/250 |
| 4,689,043 | 8/1987 | Bisha . |
| 4,802,650 | 2/1989 | Stricker .................. 604/250 |
| 4,818,190 | 4/1989 | Pelmulder et al. . |
| 4,944,485 | 7/1990 | Daoud et al. .................... 251/9 |
| 4,944,485 | 7/1990 | Daoud et al. .................... 251/9 |
| 5,017,192 | 5/1991 | Dodge et al. .............. 604/250 |
| 5,035,399 | 7/1991 | Rantanen-Lee .......... 604/250 |
| 5,201,711 | 4/1993 | Pasqualucci et al. ......... 604/153 |

FOREIGN PATENT DOCUMENTS

| | | |
|---|---|---|
| 0415021 | 2/1991 | European Pat. Off. . |
| 2590645 | 5/1987 | France ................ 604/250 |
| 2743239 | 4/1979 | Germany . |
| 1225812 | 3/1971 | United Kingdom . |

FREE FLOW PREVENTION SYSTEM FOR INFUSION PUMP

This is a continuation of application Ser. No. 07/690,819 filed Apr. 23, 1991 now abandoned.

The invention relates generally to infusion pumps and IV tubing sets for the controlled delivery of fluids to a patient, and more particularly to a free flow prevention system for preventing the free flow of fluid through the IV tubing when the tubing is disconnected from the pump.

BACKGROUND OF THE INVENTION

Infusion pumps are typically used to regulate the delivery of fluids, which may include potentially hazardous drugs, to a patient with a high degree of accuracy. Ordinarily, a roller clamp is moved to a closed position to stop flow through IV tubing before the tubing is removed from an infusion pump in order to prevent a situation that is sometimes referred to as "free flow" or "fluid runaway", that is, where the fluid is free to flow rapidly through the IV tubing without regulation by the infusion pump. Such roller clamps are effective in preventing free flow only when they are manually moved to their closed positions, and free flow or fluid runaway may occur if the roller clamp is inadvertently left in its open position. As a result, an automatic free flow prevention system is now desired wherein fluid runaway is prevented regardless of whether the pump operator remembers to close a roller or slide clamp.

One approach is described in coassigned U.S. Pat. No. 4,585,441 wherein an interlock is provided to prevent removal of the IV set unless fluid flow through the tubing is stopped. The pump operator must manually close a clamp to stop fluid flow through the tubing before the infusion pump will permit removal of the IV set.

A permanent clamp may be provided on the infusion pump from which the IV set must be manually disconnected during removal of the IV set from the infusion pump. That approach reduces the risk of fluid runaway because the permanent clamp reduces the possibility of thoughtless removal of the IV set from the infusion pump. The act of disconnecting the IV set from the permanent clamp tends to remind the operator of the need to close the roller or slide clamp on the IV set; however, it does not eliminate the risk that the operator will remove the IV set without first closing this clamp.

Other approaches include employing slide clamps to prevent or reduce the risk of removing the IV set without closing a clamp. U.S. Pat. Nos. 4,586,691; 4,689,043; and 4,818,190 describe employing slide clamps to prevent fluid runaway during removal of IV sets from infusion pumps.

Coassigned U.S. Pat. No. 5,017,192 describes a flexible clamp having a pair of clamping arms that are biased to a closed position to close the lumen of IV tubing. The clamping arms are moved and held in an open position by a wedge in the infusion pump to permit flow through the tubing during operation of the infusion pump. The clamping arms of the flexible clamp automatically close the tubing when the IV tubing set is removed from the infusion pump.

SUMMARY OF THE INVENTION

The invention provides a free flow prevention system adapted for preventing free flow of fluid through IV tubing when the tubing is disconnected from an infusion pump. The system is designed to be easy to use, and to automatically close the IV tubing to fluid flow when the tubing is removed from the infusion pump.

Generally, the free flow prevention system comprises an IV tubing set including IV tubing having a lumen through which fluid may be pumped for administration to a patient, and an infusion pump for controlling infusion of a fluid through the IV tubing.

The IV tubing set also includes a spring clip having a base and a spring arm extending from the base. The base and spring arm define a channel adapted to receive a portion of the IV tubing. The spring arm is resiliently biased to a closed position in which the IV tubing is squeezed between the spring arm and the base of the clip to close the lumen to prevent fluid flow. The spring arm is movable against the bias to an open position wherein the lumen of the IV tubing is allowed to open to allow flow through the lumen.

The infusion pump includes pumping means for pumping fluid through the IV tubing, and releasable holding means for releasably holding the IV tubing during operation of the infusion pump. Clip-holding means is provided in the infusion pump for releasably mounting the clip in the infusion pump, and clip-opening means is provided in the infusion pump for moving the spring arm of the clip from its closed position to the open position.

The clip-holding means and the clip-opening means are mounted in the infusion pump for movement of the clip-opening means relative to the clip held by the clip-holding means between an unloading position and an operating position. In the unloading position, the clip-opening means does not hold the spring arm in its open position. In the operating position, the clip-opening means moves the spring arm to its open position and holds the spring arm in the open position.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
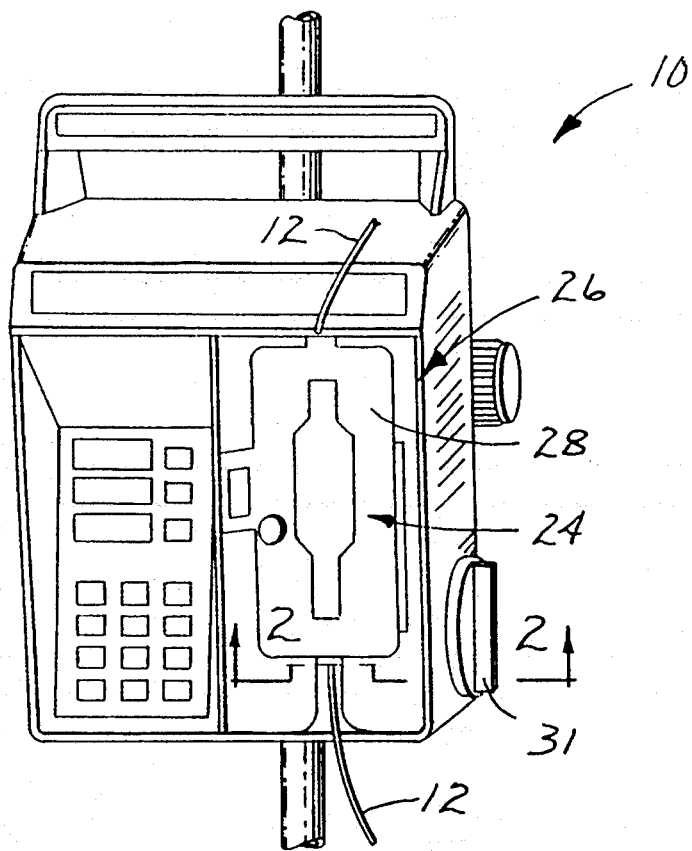
FIG. 1 is a perspective view of an infusion pump incorporating the free flow prevention system of the invention.

The free flow prevention system is particularly designed for an infusion pump 10 (FIG. 1) of the general type described in U.S. Pat. Nos. 4,236,880; 4,277,226; 4,322,201; 4,382,753; 4,391,600; 4,410,322; and U.S. Pat. No. 5,017,192 (all of which are incorporated herein by reference). Such infusion pumps are designed for use with IV tubing 12 of the type including a pumping cassette 14 having flexible walls defining fluid pumping chambers 16. The fluid pumping chambers may be compressed to regulate fluid flow through the the lumen of the IV tubing 12 without contact between the infusion pump 10 and the IV fluid.

Infusion pumps of this type are being sold by Minnesota Mining and Manufacturing Company of St. Paul, Minn. ("3M") , under various trade designations, including the "AVI 200" and "AVI 400" model series of infusion pumps. The infusion pump 10 may alternately be of the type commonly referred to as a "linear peristaltic pump", that is, pumps that selectively squeeze straight portions of the IV tubing to regulate or pump fluid through the IV tubing. In any event, the infusion pump 10 regulates fluid flow through the lumen of IV tubing 12 for administration to a patient.

As illustrated in FIGS. 2–7, a spring clip 18 is provided having a base 20 and a spring arm 22 extending from the base 20. The base 20 and spring arm 22 define a channel 23 adapted to receive a portion of the IV tubing 12, preferably a portion of the pumping cassette 14. The spring arm 22 is resiliently biased to a closed position (FIG. 2 and phantom in FIG. 6) in which the IV tubing 12 is squeezed between the spring arm 22 and the base 20 of the clip 18 to close the lumen of the IV tubing 12 to prevent fluid flow. The spring arm 22 is movable against the bias to an open position (FIG. 3 and solid in FIG. 6) wherein the lumen of the IV tubing 12 is allowed to open to allow flow through the lumen.

The infusion pump 10 includes pumping means for pumping fluid through the IV tubing, and releasable holding means 24 for releasably holding the IV tubing 12 during operation of the infusion pump 10. For example, the pumping means may include one or more pistons (not shown) that compress the pumping chambers 16 of the pumping cassette 14, and the releasable holding means 24 may be in the form of a door assembly 24. The door assembly 24 includes a door 28 mounted via a hinge to a cassette-receiving block 30 of the type described in U.S. Pat. No. 4,236,880 (incorporated herein by reference). In this example, the door assembly 24 may be moved a distance D-1 between a loading and unloading position (FIG. 2) and an operating position (FIG. 3) by turning a knob 31 extending laterally outwardly from the infusion pump 10. The loading and unloading position is forward in the infusion pump relative to the operating position, and the door 28 may be pivoted outwardly for loading and unloading of the pumping cassette 14 when the door assembly 24 is in the loading and unloading position.

Figure 2:
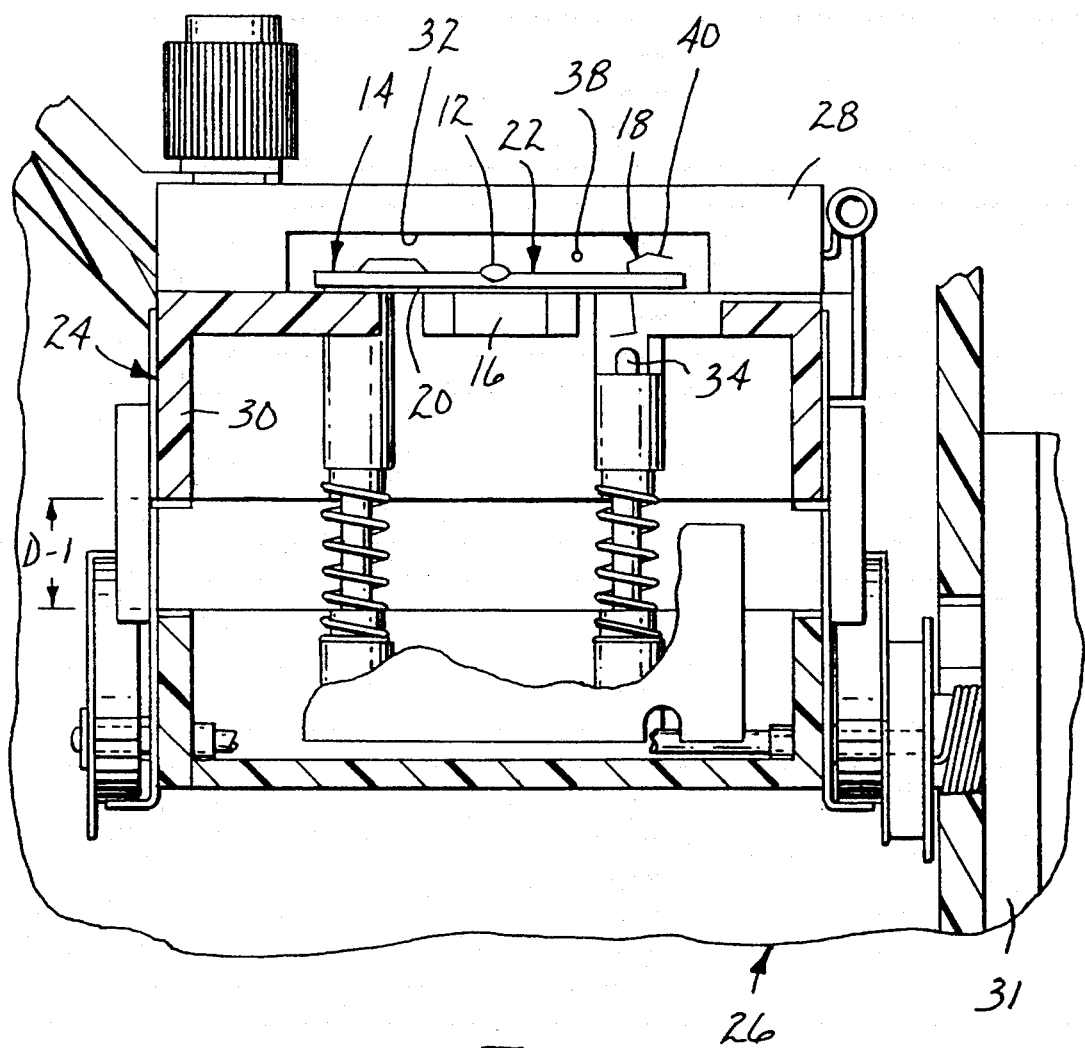
FIG. 2 is a cross-sectional view substantially along line 2—2 of FIG. 1, showing a spring clip of the free flow prevention system in its closed position.
Figure 3:
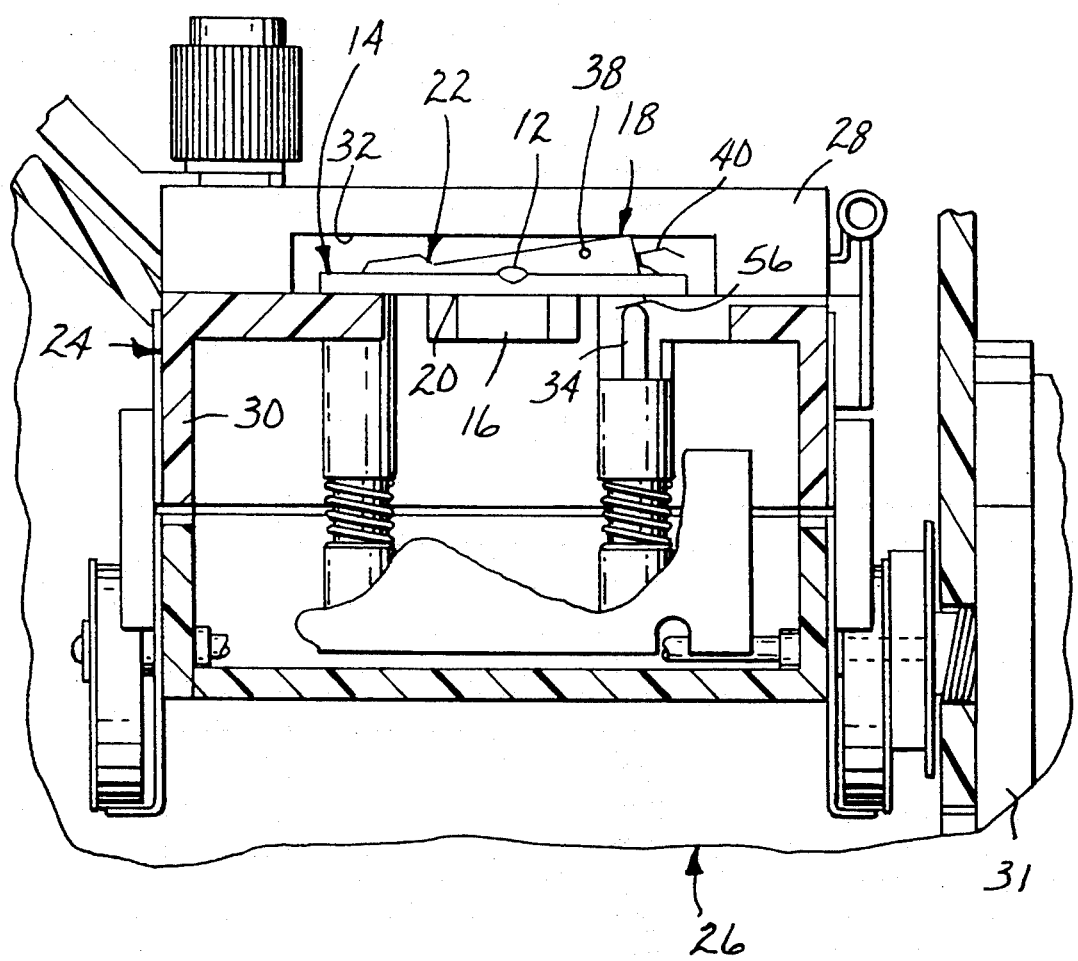
FIG. 3 is a cross-sectional view similar to FIG. 2, showing the spring clip in its open position.

Clip-receiving means, preferably including a recess 32 in the door 28, is provided for releasably receiving the spring clip 18 in the infusion pump 10, and clip-opening means, such as a pin 34, is provided for moving the spring arm 22 of the spring clip 18 from its closed position (FIG. 2) to the open position (FIG. 3). The clip-receiving means and the clip-opening pin 34 are mounted on the infusion pump 10 for movement of the clip-opening pin 34 relative to the clip 18 held by the clip-receiving means between an unloading position (FIG. 2), in which the clip-opening pin 34 does not hold the spring arm 22 in its open position, and an operating position (FIG. 3), in which the clip-opening pin 34 moves the spring arm 22 to its open position and holds the spring arm 22 in the open position.

The spring clip 18 may be both loaded into and unloaded from infusion pumps 10 of the type described in the incorporated patents with the clip-opening pin 34 and clip-receiving means in their "unloading" position. In this type of pump (as well as some others), the clip-receiving means is mounted on or formed in the door 28 and/or cassette-receiving block 30, and the clip-opening pin 34 is mounted in the main body 26 of the infusion pump 10. In this arrangement, the releasable holding means 24 is movable to move the clip-receiving means and spring clip 18 relative to the clip-opening pin 34 between the unloading and operating positions. The cassette-receiving block 30 may include one or more cylinders for receiving the pumping chambers 16 of the pumping cassette 14 and pistons (not shown) of the pumping means.

Figure 6:
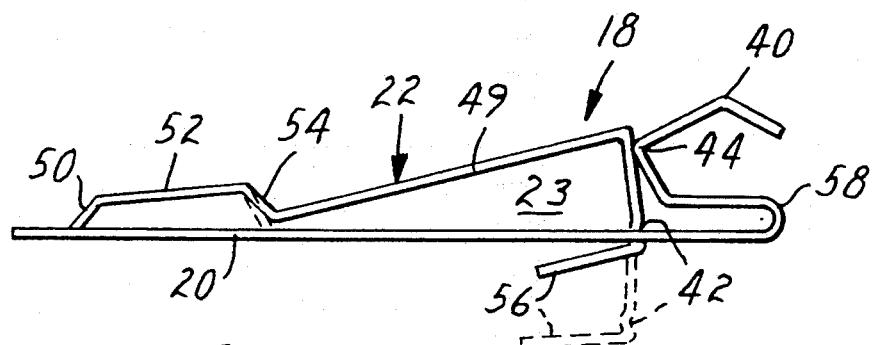
FIG. 6 is a side view of the of the spring clip of FIG. 5, showing the spring clip in its open position and illustrating the closed position in phantom.

Preferably, the spring clip 18 includes detent means 36 for releasably holding the spring arm 22 against its spring bias in a priming position (FIG. 7) in which the lumen of the IV tubing 12 is open to allow flow through the lumen. Release means, such as a resilient release spring 38 (e.g. of metal wire), is provided in the door 28 of the infusion pump 10 for releasing the spring arm 22 from the detent means 36 so that the spring arm 22 moves from its priming position (FIG. 7) toward the open and closed positions (FIGS. 2–3 and 6).

For example, the release spring 38 may be mounted in the recess 32 of the door 28 and adapted to engage the spring arm 22 when the door is in its closed position (FIGS. 1–3) to release the spring arm 22 from the detent means 36 and to move the spring arm 22 to the closed position (FIG. 2). More specifically, the spring arm 22 is spaced farther from the base 20 in the priming position (FIG. 7) than in the open position (solid in FIG. 6), and the release spring 38 is adapted to move the spring arm 22 toward the base 20 when the door 28 is moved to its closed position. So long as the door 28 is closed, the release spring 38 will tend to urge the spring arm 22 toward its closed position. The clip-opening pin 34 is adapted to move the spring arm 22 against the bias of the release spring 38 when the clip-opening pin 34 and releasable holding means 24 are in their operating position.

Figure 7:
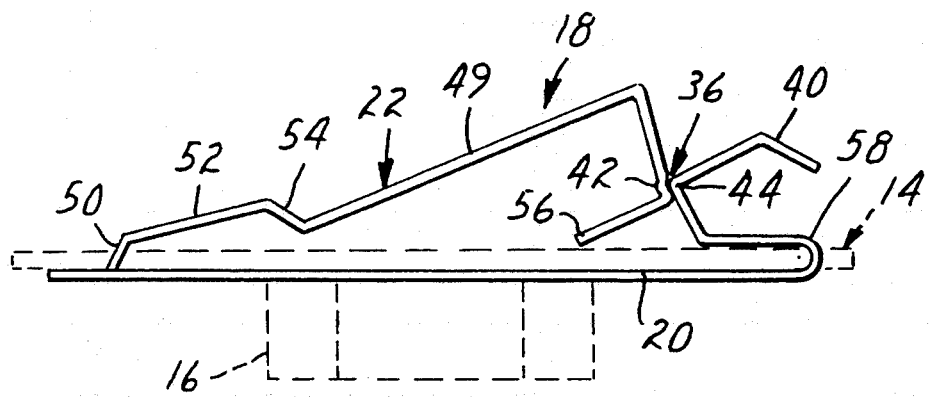
FIG. 7 is a side view similar to FIG. 6, showing the spring clip in its priming position.

The detent means 36 preferably comprises a latching arm 40 on the base 20 of the spring clip 18 adapted to engage the free end (at 36) of the spring arm 22 to hold the spring arm 22 in its priming position (FIG. 7). More particularly, the detent means 36 may comprise complementary bends in the latching arm 40 and spring arm 22 adapted to engage each other to hold the spring arm 22 in its priming position. For example, the complementary bends of the latching arm 40 and spring arm 22 may include a concave bend 42 on the free end of the spring arm 22 with its concave surface (at 42) facing the latching arm 40, and a convex bend 44 on the latching arm 40 complementary to the concave surface 42 of the spring arm 22. The convex surface 44 of the latching arm 40 is adapted for engagement with the concave surface 42 of the spring arm 22 to hold the spring arm 22 in its priming position.

Figure 4:
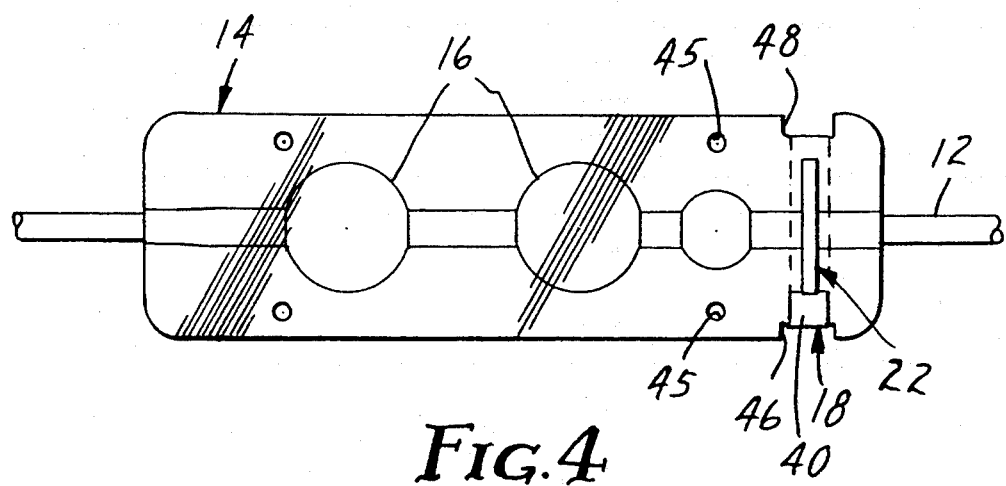
FIG. 4 is an enlarged front view of a pumping cassette having a spring clip mounted thereon.
Figure 5:
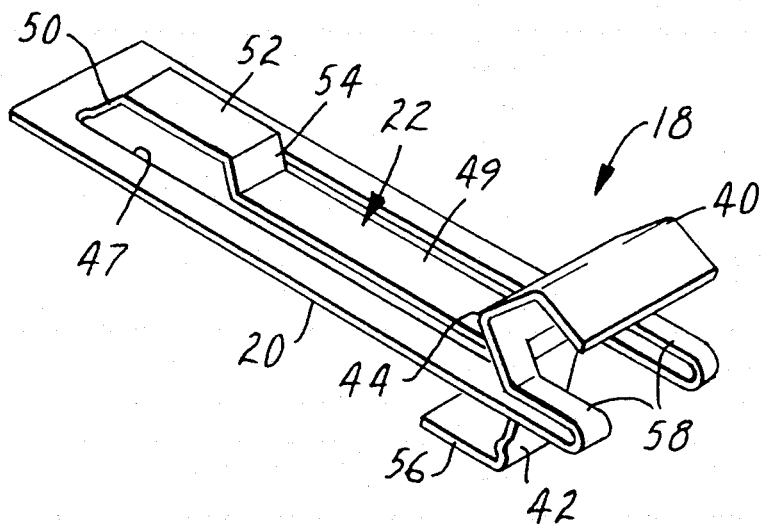
FIG. 5 is an enlarged perspective view of the spring clip of FIGS. 2-4, showing the spring clip in its closed position.

As illustrated in FIG. 4, the pumping cassette 16 may have a plurality of alignment openings 45 (e.g., four) that are adapted to receive corresponding alignment pins (not shown) extending from the cassette-receiving block 30 to properly align the pumping cassette 14 with respect to the infusion pump 10. When the pumping cassette 14 is in position on the alignment pins, (a) the pumping chambers 16 of the pumping cassette are positioned within or adjacent the piston-receiving cylinders of the cassette-receiving block 30 for operation of the pistons on the pumping chambers 16; (b) the spring clip 18 is held in proper orientation with respect to the clip-opening pin 34 so that the clip-opening pin 34 can move the spring arm 22 to its open position; (c) the spring arm 22 of the spring clip 18 will be received in the recess 32 in the door 28 when the door 28 is closed; and (d) the release spring 38 will engage the spring arm 22 when the door 28 is closed to urge the spring arm 22 from the priming position toward the closed position.

The pumping cassette 14 most preferably has two openings or slots 46 and 48 through the opposite surfaces thereof, which are arranged along opposite sides of the lumen and sealed with respect to the lumen to prevent fluid communication between the slots 46,48 and the lumen. The base 20 of the spring clip 18 extends along one surface (not shown in FIG. 4) of the pumping cassette 14 between the two slots 46 and 48. The spring arm 22 extends from the base 20 through one of the slots 46 and along the pumping cassette 14 toward the other slot 48 such that the spring arm 22 engages the pumping cassette 14 when in its closed position to close the lumen to fluid flow. The latching arm 40 of the spring clip 18 extends from base 20 through slot 48 of the pumping cassette 14. This arrangement is believed to be advantageous in that the spring clip 18 is securely held on the pumping cassette 14 in proper position with respect to the lumen, and in alignment with the clip-opening pin 34 and clip-receiving means when the pumping cassette 14 is placed on the alignment pins on the cassette-receiving block 30.

Preferably, the spring clip 18 is formed from a single flat sheet of resilient stainless steel cut and bent to form the spring arm 22, latching arm 40 and base 20 of the spring clip 18, although it has also been contemplated to form the spring clip 18 from thermoplastic or thermoset resin. In the example of a spring clip 18 cut and bent from a single metal sheet, the process of producing the clip 22 forms a longitudinal slot 47 (FIG. 5) along the base 20 of the clip 18 having a width that is the same or preferably larger than the width of the spring arm 22. It is contemplated that the longitudinal slot 47 of the spring clip 18 may extend into the latching arm 40 to some extent but preferably not past the convex bend 44.

Before discussing further details of a preferred spring clip 18, nomenclature relating to directions along the clip 18 will be defined. The base 20 of the spring clip 18 may be viewed as defining a longitudinal direction (rightwardly and leftwardly in FIGS. 6 and 7), and the spring arm 22 may be viewed as being movable in a lateral plane (upwardly or downwardly in FIGS. 6 and 7) between the priming, open and closed positions. The direction of movement of the spring arm 22 from the priming position (FIG. 7) toward the closed position (phantom in FIG. 6) constitutes the laterally inward direction (downwardly in FIGS. 6 and 7), and the opposite direction constitutes the laterally outward direction.

Most preferably, the spring arm 22 extends from generally adjacent one end of the base 20 generally longitudinally along the base 20 toward the latching arm 40. The spring arm 22 terminates in a free end (at 36) generally adjacent the latching arm 40. The spring arm 22 has a bent section integrally connecting the main section 49 of the spring arm 22 to the base 20. The bent section of the spring arm 22 includes a first portion 50 bent laterally outwardly from the base 18, a second portion 52 bent laterally inwardly from the first portion 50 and extending generally longitudinally along the base 20 when the spring arm 22 is in its closed position, and a third portion 54 bent laterally inwardly from the second portion 52. The spring arm 22 has a straight main section 49 bent laterally outwardly from the third portion 54 such that the main section 49 extends in the direction generally parallel with the second portion 52 of the spring arm 22.

The free end 36 of the preferred spring arm 22 has a detent portion (at 42) bent laterally inwardly from the main section 49 and adapted for sliding engagement with the latching arm 40. The detent portion 42 includes the concave bend 42 that provides part of the detent means. The free end 36 of the spring arm 22 also including a tab portion 56 bent from the detent portion 42 and adapted to be engaged by the clip-opening pin 34 to move the spring arm 22 from its closed position to its open position. The tab portion 56 extends in a direction generally parallel to the longitudinal direction when the spring arm 22 is in its closed position, and the concave bend 42 of the detent portion 42 is generally adjacent the tab portion 56 so that the priming position is laterally outwardly of the open and closed positions of the spring clip 22. The tab portion 56 preferably extends in the direction generally away from the latching arm 40 and generally parallel with the main portion 49 of the spring arm.

The latching arm 40 preferably includes a first section 58 extending from the end of the base 20 opposite the spring arm 22 generally longitudinally along the base 20, and a second section (at 44) bent laterally outwardly from the first section 58. The second section 44 of the latching arm 40 includes the convex bend 44 that is complementary to the concave bend 42 of the spring arm 22.

OPERATION

Operation of the free flow prevention system will be described with reference to the preferred embodiment having a pumping cassette 14 for purposes of illustration. The IV tubing set is preferably provided in sterile packaging (not shown), with the spring clip 20 in its priming position so that the IV tubing 12 (including the pumping cassette 14) can be readily charged with fluid and air bubbles removed. The pumping cassette 14 and the spring clip 18 are then manually placed or inserted into the cassette-receiving block 30.

The door 28 of the door assembly 24 is closed to hold the spring clip 18, pumping cassette 14 and IV tubing 12 in the door assembly 24. As the door 28 is closed, the release spring 38 is forced against the spring arm 22 of the spring clip 18 to push the spring arm 22 from its detented priming position and into the closed position (FIG. 2), in which fluid flow through the IV tubing 12 is blocked prior to initiating the operation of the infusion pump 10.

The knob 31 is then turned to draw the door assembly 24 toward the main body 26 of the infusion pump 10. As the door assembly 24 is drawn toward the main body 26 of the infusion pump 10, the clip-opening pin 34 is forced against the tab portion 56 of the spring arm 22 to move it against the bias of the release spring 38 into the open position (FIG. 3) to permit fluid flow through the IV tubing 12 during operation of the pump 10. The infusion pump 10 may then be operated in the normal manner to control the delivery of fluid to a patient.

In order to remove the IV tubing set from the infusion pump 10, the knob 31 is turned in the opposite direction to return the door assembly 24 to its loading and unloading position (FIG. 2), which in the example is forward (upwardly in FIGS. 2 and 3) of the operating position. As this occurs, the opening force provided by the clip-opening pin 34 is removed, and the bias of the release spring 38 and the bias of the spring arm 22 return the spring arm 22 to its closed position. At this point, the lumen through the pumping cassette 14 should be closed to fluid flow.

The door 28 is then opened, and the IV tubing set, including the IV tubing 12 and spring clip 18, are removed from the infusion pump 10. The lumen of the IV tubing 12 remains closed due to the clamping action of the spring arm 22 against the tubing 12. As a result, free flow through the tubing 12 is prevented during and after disconnection of the IV tubing set regardless of whether a standard roller or pinch clamp (not shown) is closed.

If use of the IV tubing set for gravity feed after removal from the infusion pump 10 is desired, the practitioner may manually move the spring arm 22 to its priming position to permit such flow. Of course, a conventional roller clamp (not shown) may be provided to provide some regulation of flow through the IV tubing 12 in that event.

As various changes could be made in the above constructions without departing from the scope of the invention, it is intended that all matter contained in the above description or shown in the accompanying drawing be interpreted as illustrative and not in a limiting sense.

We claim:

1. An IV tubing set through which fluid flow is regulated by an infusion pump of the type used to regulate fluid being delivered to a patient; the IV tubing set comprising:

IV tubing having a lumen through which fluid may be pumped for administration to a patient, the IV tubing including a pumping cassette having at least two flexible walls having inner surfaces defining fluid pumping chambers therebetween, the pumping chambers defining a portion of the lumen, the flexible walls defining a flange extending from the fluid pumping chambers and terminating in a peripheral edge of the pumping cassette, and further defining opposite outwardly-facing major surfaces of the pumping cassette; and a spring clip mounted on the flange of the pumping cassette and having a base and a spring arm extending therefrom along the opposite major surfaces of the pumping cassette and across the lumen, the spring arm being resiliently biased to a closed position in which the pumping cassette is squeezed between the spring arm and the base of the clip to close the lumen to prevent fluid flow, the spring arm being movable against its normal biasing force to an open position wherein the lumen of the pumping cassette is allowed to open to allow flow through the lumen;

the spring clip further comprising detent means for releasably holding the spring arm against its normal spring biasing force in a priming position in which the lumen of the IV tubing is open to allow flow through the lumen.

2. An IV tubing set according to claim 1 wherein the spring arm is spaced farther from the base in the priming position than in the open position.

3. An IV tubing set according to claim 2 wherein the spring arm has a free end, the detent means comprising a latching arm extending from the base of the spring clip adapted to engage the free end of the spring arm to hold the spring arm in its priming position.

4. An IV tubing set according to claim 3 wherein the detent means further comprises complementary bends in the latching arm and spring arm adapted to engage each other to hold the spring arm in its priming position.

5. An IV tubing set according to claim 4 wherein the complementary bends of the latching arm and spring arm include a concave bend on the free end of the spring arm with its concave surface facing the latching arm, and a convex bend on the latching arm complementary to the spring arm with its convex surface adapted for engagement with the concave surface of the spring arm to hold the spring arm in its priming position.

6. An IV tubing set according to claim 5 adapted to be used in an infusion pump having a clip-opening pin for moving the spring arm of the IV tubing set from its closed to its open position to allow fluid flow through the IV tubing set;

the base of the spring clip defining a longitudinal direction and the spring arm is movable in a lateral plane defined by the base and spring arm between the priming, open and closed positions, the direction of movement of the spring arm from the priming position toward the closed position constituting the laterally inward direction;

the spring arm extending from generally adjacent one end of the base generally longitudinally along the base toward the latching arm and terminating in its free end generally adjacent the latching arm, the spring arm having a bent portion connecting the spring arm to the base including a first portion bent laterally outwardly from the base, a second portion bent laterally inwardly from the first position and extending generally longitudinally along the base when the spring arm is in its closed position, and a third portion bent laterally inwardly from the second portion, the spring arm having a main section bent laterally outwardly from the third portion and extending in the direction generally parallel with the second portion of the spring arm;

the free end of the spring arm having a detent portion bent laterally inwardly from the main portion and adapted for sliding engagement with the latching arm, the detent portion including the concave bend, the free end of the spring arm also including a tab portion bent from the detent portion and adapted to be engaged by the clip-opening pin of the infusion pump to move the spring arm from its closed position to its open position, the tab portion extending in a direction generally parallel to the longitudinal direction when the spring arm is in its closed position, the concave bend of the detent portion being generally adjacent the tab portion; and the latching arm including a first section extending from the other end of the base generally longitudinally along the base, and a second section bent laterally outwardly from the first section, the second section including the convex bend that is complementary to the concave bend of the spring arm.

7. A free flow prevention system comprising:
an IV tubing set comprising:
  IV tubing having a lumen through which fluid may be pumped for administration to a patient; and
  a spring clip having a base and a spring arm extending therefrom, the base and spring arm defining a channel adapted to receive a portion of the IV tubing, the spring and being resiliently biased to a closed position in which the IV tubing is squeezed between the spring arm and the base of the clip to close the lumen to prevent fluid flow, the spring arm being movable against its normal biasing force to an open position wherein the lumen of the IV tubing is allowed to open to allow flow through the lumen, the spring clip further comprising detent means for releasably holding the spring arm against its normal spring biasing force in a priming position in which the lumen of the IV tubing is open to allow flow through the lumen; and
an infusion pump for controlling infusion of a fluid through the IV tubing, the infusion pump comprising:
  pumping means for pumping fluid through the IV tubing:
  releasable holding means for releasably holding the IV tubing during operation of the infusion pump;
  clip-receiving means for releasably receiving the clip in the infusion pump: and
  clip-opening means for moving the spring arm of the clip from its closed position to the open position;
  the clip-receiving means and the clip-opening means being mounted on the infusion pump for movement of the clip-opening means relative to the clip received by the clip-receiving means between an unloading position, in which the clip-opening means does not hold the spring arm in its open position and an operating position, in which the clip-opening means moves the spring arm to its open position and holds the spring arm in the open position;
  the clip-opening means comprising a clip-opening pin mounted in the infusion pump for engagement with the spring arm of the spring clip, the pin and the spring clip being movable relative to one another between the operating position, in which the pin engages the spring arm to hold the spring arm in its open position, and the unloading position, in which the pin is not holding the spring arm in its open position so that the spring arm is allowed to move to its closed position to close the lumen of the IV tubing;
  the releasable holding means including a door mounted on the infusion pump, the clip-receiving means including walls within the door defining a recess for receiving the spring am of the spring clip and allowing movement of the spring arm between its open and closed positions;
  the system further comprising release means in the door for releasing the detent means before operation of the infusion pump so that the spring arm moves from its priming position toward the open and closed positions:
  the door having open and closed positions, the release means comprising a resilient release spring mounted in the recess of the door and adapted to engage the spring arm to release the detent means and move the spring arm to the closed position when the door is moved to its closed position, the clip-opening pin being adapted to move the spring arm against the bias of the release spring when the clip-opening pin and releasable holding means are in their operating position.

8. A system according to claim 7 wherein the spring arm is spaced farther from the base in the priming position than in the open position, the release spring being adapted to move the spring arm toward the base when the door is moved to its closed position.

9. A system according to claim 8 wherein the spring arm has a free end, the detent means comprising a latching arm on the base of the spring clip adapted to engage the free end of the spring arm to hold the spring arm in its priming position.

10. A system according to claim 9 wherein the detent means further comprises complementary bends in the latching arm and spring arm adapted to engage each other to hold the spring arm in its priming position.

11. A system according to claim 10 wherein the complementary bends of the latching arm and spring arm include a concave bend on the free end of the spring arm with its concave surface facing the latching arm, and a convex bend on the latching arm complementary to the spring arm with its convex surface adapted for engagement with the concave surface of the spring arm to hold the spring arm in its priming position.

12. A system according to claim 11 wherein the IV tubing includes a pumping cassette having flexible walls defining fluid pumping chambers that may be compressed by the pumping means to regulate fluid flow through the IV tubing, the door being adapted to hold the pumping cassette in the infusion pump.

13. A system according to claim 12 wherein the spring clip is formed from a flat sheet of resilient metal cut and bent to form the spring arm, latching arm and base of the spring clip.

14. A free flow prevention system comprising:
an IV tubing set comprising:
  IV tubing having a lumen through which fluid may be pumped for administration to a patient, the IV tubing including a pumping cassette having at least two flexible walls defining fluid pumping chambers therebetween and a flange extending from the fluid pumping chambers and terminating in a peripheral edge of the pumping cassette, the pumping chambers defining a portion of the lumen, the flexible walls also defining opposite outwardly-facing major surfaces of the pumping cassette; and
  a spring clip mounted on the flange of the pumping cassette and having a base and a spring arm extending therefrom along the opposite major surfaces of the pumping cassette and across the lumen, the spring arm being resiliently biased to a closed position in which the pumping cassette is squeezed between the spring arm and the base of the clip to close the lumen to prevent fluid flow, the spring arm being movable against its normal biasing force to an open position wherein the lumen of the pumping cassette is allowed to open to allow flow through the lumen; and an infusion pump for controlling infusion of a fluid through the IV tubing, the infusion pump comprising:

pumping means for pumping fluid through the pumping cassette;

releasable holding means for releasably holding the pumping cassette during operation of the infusion pump;

clip-receiving means for releasably receiving the clip in the infusion pump; and clip-opening means for moving the spring arm of the clip from its closed position to the open position;

the clip-receiving means and the clip-opening means being mounted on the infusion pump for movement of the clip-opening means relative to the clip received by the clip-receiving means between an unloading position, in which the clip-opening means does not hold the spring arm in its open position, and an operating position, in which the clip-opening means moves the spring arm to its open position and holds the spring arm in the open position.

15. A system according to claim 14 wherein the clip-opening means comprises a clip-opening pin mounted in the infusion pump for engagement with the spring arm of the spring clip, the pin and the spring clip being movable relative to one another between the operating position, in which the pin engages the spring arm to hold the spring arm in its open position, and the unloading position, in which the pin is not holding the spring arm in its open position so that the spring arm is allowed to move to its closed position to close the lumen of the IV tubing.

16. A system according to claim 15 wherein the clip-receiving means is mounted on or formed in the releasable holding means, the releasable holding means being movable to move the clip-holding means relative to the pin between the unloading and operating positions.

17. A system according to claim 15 wherein the releasable holding means includes a door mounted on the infusion pump, the clip-receiving means including walls within the door defining a recess for receiving the spring arm of the spring clip and allowing movement of the spring arm between its open and closed positions.

18. A system according to claim 1 wherein the peripheral edges of the pumping cassette include opposite lateral edges extending along opposite sides of the lumen, and the flange of the pumping cassette has opposed slots extending inwardly toward each other along the opposite outwardly-facing major surfaces from opposite lateral edges of the pumping cassette, the spring clip being held in position across the lumen of the pumping cassette by the opposed slots.

19. A free flow prevention system comprising:

an IV tubing set comprising:

IV tubing having a lumen through which fluid may be pumped for administration to a patient; and a spring clip having a base and a spring arm extending therefrom, the base and spring arm defining a channel adapted to receive a portion of the IV tubing, the spring arm being resiliently biased to a closed position in which the IV tubing is squeezed between the spring arm and the base of the clip to close the lumen to prevent fluid flow, the spring arm being movable against its normal biasing force to an open position wherein the spring arm is spaced from the base of the spring clips such that the lumen of the IV tubing is allowed to open to allow flow through the lumen, the spring clip further comprising detent means for releasably holding the spring arm against its normal spring biasing force in a priming position in which the spring arm is farther spaced from the base of the spring clip than in the open position and the lumen of the IV tubing is open to allow flow through the lumen; and an infusion pump for controlling infusion of a fluid through the IV tubing, the infusion pump comprising:

pumping means for pumping fluid through the IV tubing;

releasable holding means for releasably holding the IV tubing during operation of the infusion pump;

clip-receiving means for releasably receiving the clip in the infusion pump; and clip-opening means for moving the spring arm of the clip from its closed position to the open position;

the clip-receiving means and the clip-opening means being mounted on the infusion pump for movement of the clip-opening means relative to the clip received by the clip-receiving means between an unloading position, in which the clip-opening means does not hold the spring arm in its open position, and an operating position, in which the clip-opening means moves the spring arm to its open position and holds the spring arm in the open position;

the clip-opening means comprising a clip-opening pin mounted in the infusion pump for engagement with the spring arm of the spring clip, the pin and the spring clip being movable relative to one another between the operating position, in which the pin engages the spring arm to hold the spring arm in its open position, and the unloading position, in which the pin is not holding the spring arm in its open position so that the spring arm is allowed to move to its closed position to close the lumen of the IV tubing;

the releasable holding means including a door mounted on the infusion pump, the clip-receiving means including walls within the door defining a recess for receiving the spring arm of the spring clip and allowing movement of the spring arm between its open and closed positions.

20. A system according to claim 19 further comprising release means in the door for releasing the detent means before operation of the infusion pump so that the spring arm moves from its priming position toward the open and closed positions.

21. An infusion pump for regulating fluid flow through a lumen of an IV tubing set to a patient, the IV tubing set being of the type including a spring clip having a base and a spring arm extending therefrom, the base and spring arm defining a channel adapted to receive a portion of the IV tubing, the spring arm being resiliently biased to a closed position in which the IV tubing is squeezed between the spring arm and the base of the clip to close the lumen to prevent fluid flow, the spring arm being movable against its normal biasing force to an open position wherein the lumen of the IV tubing is allowed to open to allow flow through the lumen, the spring clip including detent means for releasably holding the spring arm of the spring clip against its normal spring biasing force in a priming position in which the lumen of the IV tubing is open to allow flow through the lumen; the infusion pump comprising:

pumping means for pumping fluid through the IV tubing;

releasable holding means adapted for releasably holding the IV tubing during operation of the infusion pump;

clip-receiving means adapted for releasably receiving the spring clip in the infusion pump; and clip-opening means adapted for moving the spring arm of the spring clip from its closed position to the open position;

the clip-receiving means and the clip-opening means being mounted on the infusion pump for movement of the clip-opening means relative to the clip received by the clip-receiving means between an unloading position, in which the clip-opening means does not hold the spring arm in its open position, and an operating position, in which the clip-opening means moves the spring arm to its open position and holds the spring arm in the open position;

the clip-opening means comprising a clip-opening pin mounted in the infusion pump for engagement with the spring arm of the spring clip, the pin and the clip-receiving means being movable relative to one another between the operating position, in which the pin is adapted to engage the spring arm to hold the spring arm in its open position, and the unloading position, in which the pin is adapted not to hold the spring arm in its open position so that the spring arm is allowed to move to its closed position to close the lumen of the IV tubing;

the releasable holding means including a door mounted on the infusion pump, the clip-receiving means including walls within the door defining a recess adapted for receiving the spring arm of the spring clip and allowing movement of the spring arm between its open and closed positions;

the infusion pump further comprising release means in the door adapted for releasing the detent means before operation of the infusion pump so that the spring arm moves from its priming position toward the open and closed positions;

the door having open and closed positions, the release means comprising a resilient release spring mounted in the recess of the door and adapted to engage the spring arm of the spring clip to release the detent means and move the spring arm to the closed position when the door is moved to its closed position, the clip-opening pin being adapted to move the spring arm against the bias of the release spring when the clip-opening pin and releasable holding means are in their operating position.

22. An infusion pump according to claim 21 adapted for use with an IV tubing set of the type including a pumping cassette having flexible walls defining fluid pumping chambers that may be compressed by the pumping means to regulate fluid flow through the IV tubing; the releasable holding means of the infusion pump including cassette-receiving means adapted for receiving the pumping cassette, the door constituting a part of the cassette-receiving means, the pumping means including means adapted for compressing the pumping chambers of the pumping cassette to regulate fluid flow through the IV tubing set.

23. An IV tubing set through which fluid flow is regulated by an infusion pump of the type used to regulate fluid being delivered to a patient; the IV tubing set comprising:

IV tubing having a lumen through which fluid may be pumped for administration to a patient, the IV tubing including a pumping cassette having at least two flexible walls having inner surfaces defining fluid pumping chambers therebetween, the pumping chambers defining a portion of the lumen, the flexible walls defining a flange extending from the fluid pumping chambers and terminating in a peripheral edge of the pumping cassette, and further defining opposite outwardly-facing major surfaces of the pumping cassette; and a spring clip mounted on the flange of the pumping cassette and having a base and a spring arm extending therefrom along the opposite major surfaces of the pumping cassette and across the lumen, the spring arm being resiliently biased to a closed position in which the pumping cassette is squeezed between the spring arm and the base of the clip to close the lumen to prevent fluid flow, the spring arm being movable against its normal biasing force to an open position wherein the lumen of the pumping cassette is allowed to open to allow flow through the lumen.

24. An IV tubing set according to claim 23 wherein the peripheral edges of the pumping cassette include opposite lateral edges extending along opposite sides of the lumen, and the flange of the pumping cassette has opposed slots extending inwardly toward each other along the opposite outwardly-facing major surfaces from the opposite lateral edges of the pumping cassette, the spring clip being held in position across the lumen of the pumping cassette by the opposed slots.

25. An IV tubing set through which fluid flow is regulated by an infusion pump of the type used to regulate fluid being delivered to a patient, the infusion pump having pumping means for regulating fluid flow through the tubing set; the IV tubing set comprising:

IV tubing having a lumen through which fluid may be pumped for administration to a patient; and a spring clip having a base and a spring arm extending therefrom, the base and spring and defining a channel adapted to receive a portion of the IV tubing, the spring arm being resiliently biased to a closed position in which the IV tubing is squeezed between the spring arm and the base of the clip to close the lumen to prevent fluid flow, the spring arm being movable against its normal biasing force to an open position wherein the lumen of the IV tubing is allowed to open to allow flow through the lumen, the spring arm being spaced farther from the base in the priming position than in the open position, the spring arm having a free end;

the spring clip further comprising detent means for releasably holding the spring arm against its normal spring biasing force in a priming position in which the lumen of the IV tubing is open to allow flow through the lumen, the detent means comprising a latching arm extending from the base of the spring clip adapted to engage the free end of the spring arm to hold the spring arm in its priming position, the detent means further comprising complementary bends in the latching arm and spring arm adapted to engage each other to hold the spring arm in its priming position;

the IV tubing including a pumping cassette having at least two flexible walls having inside surfaces defining fluid pumping chambers therebetween, the pumping chambers defining a portion of the lumen, the flexible walls further defining a flange extending from the fluid pumping chambers and terminating in a peripheral edge of the pumping cassette, the flexible walls further having outer major surfaces defining opposite outwardly-facing major surfaces of the pumping cassette, the pumping chambers being adapted to be compressed by the pumping means of the infusion pump to regulate fluid flow through the lumen of the IV tubing, the spring arm and base of the spring clip being mounted on the flange of the pumping cassette.

26. An IV tubing set according to claim 25 wherein the pumping cassette has two openings or slots through the opposite surfaces thereof, arranged along opposite sides of the lumen and sealed with respect to the lumen to prevent fluid communication between the openings or slots and the lumen, the base of the spring clip extending along one surface of the pumping cassette between the two openings or slots, the spring arm extending from the base through one of the openings or slots and along the pumping cassette toward the other opening or slot such that the spring arm engages the pumping cassette when in its closed position to close the lumen to fluid flow, and the latching arm of the spring clip extending from the base through the other opening or slot.

27. An IV tubing set according to claim 25 wherein the spring clip is formed from a flat sheet of resilient metal cut and bent to form the spring arm, latching arm and base of the spring clip.

28. A spring clip for preventing undesired free flow of fluid through IV tubing of the type having a lumen through which fluid flow is regulated by an infusion pump having pumping means to regulate fluid being delivered to a patient, the spring clip comprising a base and a spring arm extending therefrom, the base and spring arm defining a channel adapted to receive a portion of the IV tubing, the spring arm being resiliently biased to a closed position in which the IV tubing is squeezed between the spring arm and the base of the clip to close the lumen to prevent fluid flow, the spring arm being movable against its normal biasing force to an open position in which the lumen of the IV tubing is allowed to open to allow flow through the lumen, the spring clip further comprising detent means for releasably holding the spring arm against its normal spring biasing force in a priming position in which the spring arm is spaced farther from the base in the priming position than in the open position so that the lumen of the IV tubing is open to allow flow through the lumen;

the spring arm having a free end, the detent means comprising a latching arm on the base of the spring clip adapted to engage the free end of the spring arm to hold the spring arm in its priming position;

the detent means further comprising complementary bends in the latching arm and spring arm adapted to engage each other to hold the spring arm in its priming position;

the base of the spring clip defining a longitudinal direction and the spring arm is movable in a lateral plane defined by the base and spring arm between the priming, open and closed positions, the direction of movement of the spring arm from the priming position toward the closed position constituting the laterally inward direction;

the complementary bends of the latching arm and spring arm including a concave bend on the free end of the spring arm with its concave surface facing the latching arm, and a convex bend on the latching arm complementary to the spring arm with its convex surface adapted for engagement with the concave surface of the spring arm to hold the spring arm in its priming position;

the spring arm extending from generally adjacent one end of the base generally longitudinally along the base toward the latching arm and terminating in its free end generally adjacent the latching arm, the spring arm having a bent portion connecting the spring arm to the base including a first portion bent laterally outwardly from the base, a second portion bent laterally inwardly from the first portion and extending generally longitudinally along the base when the spring arm is in its closed position, and a third portion bent laterally inwardly from the second portion, the spring arm having a main section bent laterally outwardly from the third portion and extending in the direction generally parallel with the second portion of the spring arm;

the free end of the spring arm having a detent portion bent laterally inwardly from the main portion and adapted for sliding engagement with the latching arm, the detent portion including the concave bend, the free end of the spring arm also including a tab portion bent from the detent portion and adapted to be engaged by a clip-opening pin in the infusion pump to move the spring arm from its closed position to its open position, the tab portion extending in a direction generally parallel to the longitudinal direction when the spring arm is in its closed position, the concave bend of the detent portion being generally adjacent the tab portion; and the latching arm including a first section extending from the other end of the base generally longitudinally along the base, and a second section bent laterally outwardly from the first section, the second section including the convex bend that is complementary to the concave bend of the spring arm.

29. A spring clip according to claim 28 wherein the spring clip is formed from a flat sheet of spring steel cut and bent to form the spring arm, latching arm and base of the spring clip.

* * * * *

UNITED STATES PATENT AND TRADEMARK OFFICE
CERTIFICATE OF CORRECTION

PATENT NO. : 5,437,642

DATED : August 1, 1995

INVENTOR(S) : Gary A. Thill, Mark A. Toycen, Kent R. Struble and Timothy G. Curran It is certified that error appears in the above-indentified patent and that said Letters Patent is hereby corrected as shown below:

Col. 9, line 16, "and" should read --arm--.

Col. 9, line 48, after "position" insert --,--.

Col. 11, line 56, "1" should read --14--.

Signed and Sealed this

Sixteenth Day of April, 1996

*Attest:*

BRUCE LEHMAN

*Attesting Officer*     *Commissioner of Patents and Trademarks*